(12) United States Patent
Rudnick et al.

(10) Patent No.: US 6,319,277 B1
(45) Date of Patent: *Nov. 20, 2001

(54) NESTED STENT

(75) Inventors: James J. Rudnick, Waldwick; Dominik M. Wiktor, Cranford, both of NJ (US)

(73) Assignee: Meadox Medicals, Inc., Oakland, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/271,304

(22) Filed: Mar. 17, 1999

Related U.S. Application Data (63) Continuation of application No. 08/708,651, filed on Sep. 5, 1996, now Pat. No. 5,906,639, which is a continuation of application No. 08/289,791, filed on Aug. 12, 1994, now Pat. No. 5,575,816.

(51) Int. Cl.[7] .................................................. A61F 2/06
(52) U.S. Cl. .......................................... 623/1.13; 623/1.22
(58) Field of Search .................................. 623/1, 11, 12; 606/191, 194, 198

(56) References Cited

U.S. PATENT DOCUMENTS

| 5,643,312 | 7/1997 | Fischell et al. . |
| 5,876,432 | 3/1999 | Lau et al. . |
| 5,879,370 | 3/1999 | Fischell et al. . |

*Primary Examiner*—David J. Isabella
(74) *Attorney, Agent, or Firm*—Hoffmann & Baron, LLP (57) ABSTRACT

An intraluminally implantable stent is formed of helically wound wire. The stent has a generally elongate tubular configuration and is radially expandable after implantation in a body vessel. The wire includes successively formed waves along the length of the wire. When helically wound into a tube, the waves are longitudinally nested along the longitudinal extent of the stent so as to form a densely compacted wire configuration. After radial expansion the stent maintains high radial compressive strength and wire density to retard tissue ingrowth.

85 Claims, 3 Drawing Sheets

NESTED STENT

This application is a continuation of U.S. application Ser. No. 08/708,651, filed on Sep. 5, 1996 now U.S. Pat. No. 5,906,639, which is a continuation of U.S. application Ser. No. 08/289,791, filed on Aug. 12, 1994, which is now U.S. Pat. No. 5,575,816.

FIELD OF THE INVENTION

The present invention relates generally to implantable intraluminal stents and more particularly, the present invention relates to an improved high strength intraluminal stent having increased wire density.

BACKGROUND OF THE INVENTION

It is well known to employ endoprostheses for the treatment of diseases of various body vessels. Intraluminal devices of this type are commonly referred to as stents. These devices are typically intraluminally implanted by use of a catheter into various body organs such as the vascular system, the bile tract and the urogenital tract. Many of the stents are radially compressible and expandable so that they may be easily inserted through the lumen in a collapsed or unexpanded state. Some stent designs are generally flexible so they can be easily maneuvered through the various body vessels for deployment. Once in position, the stent may be deployed by allowing the stent to expand to its uncompressed state or by expanding the stent by use of a catheter balloon.

As stents are normally employed to hold open an otherwise blocked, constricted or occluded lumen; a stent must exhibit a relatively high degree of radial or hoop strength in its expanded state. The need for such high strength stents is especially seen in stents used in the urogenital or bile tracts where disease or growth adjacent the lumen may exert an external compressive force thereon which would tend to close the lumen.

One particular form of stent currently being used is a wire stent. Stents of this type are formed by single or multiple strands of wire which may be formed into a shape such as a mesh coil, helix or the like which is flexible and readily expandable. The spaces between the coiled wire permit such flexibility and expansion. However, in certain situations, such as when the stent is employed in the urogenital or bile tract, it is also desirable to inhibit tissue ingrowth through the stent. Such ingrowth through the stent could have a tendency to reclose or occlude the open lumen. The open spaces between the wires forming the stent, while facilitating flexibility and expansion, have a tendency to allow such undesirable tissue ingrowth.

Attempts have been made to provide a stent which has less open space and more solid wire. U.S. Pat. No. 5,133,732 shows a wire stent where the wire forming the stent is overlapped during formation to provide less open space. However such overlapping wire increases the diameter of the stent and has a tendency to reduce flexibility and make implantation more difficult. It is therefore desirable to provide a wire stent which exhibits high compressive strength and full flexibility without allowing extensive ingrowth therethrough.

SUMMARY OF THE INVENTION

It is an object of the present invention to provide an intraluminal stent which exhibits high compressive strength and is resistive to tissue ingrowth.

It is a further object of the present invention to provide a flexible wire stent having high compressive strength and maximum wire density to inhibit tissue ingrowth.

In the efficient attainment of these and other objects, the present invention provides an intraluminal stent including a generally elongate tubular body formed of a wound wire. The wire forming the stent is formed into successively shaped waves, the waves being helically wound along the length of the tube. The longitudinal spacing between the helical windings of the tube is formed to be less than twice the amplitude of the waves thereby resulting in a dense wire configuration.

As more particularly shown by way of the preferred embodiment herein, an intraluminal wire stent includes longitudinally adjacent waves being nested along the length of the tubular body. The peaks or apices of the longitudinally nested waves are linerally aligned. Further, the intraluminal stent so constructed would have a percentage of open surface area in relationship to the total surface area of the stent which is less than 30% in the closed state, resulting in less open area upon expansion which would inhibit tissue ingrowth.

DETAILED DESCRIPTION OF THE PREFERRED EMBODIMENTS

Figure 1:
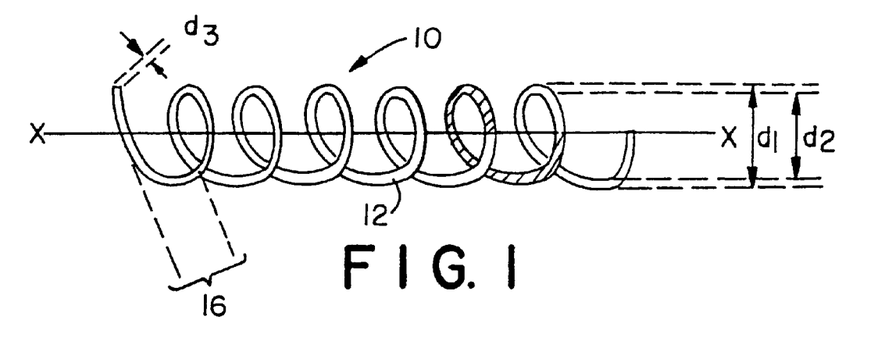
FIG. 1 is a perspective view of a conventional helical coil formed of a single wound wire.

A simple helically formed coil spring 10 is shown in FIG. 1. Coil spring 10 is formed of a single metallic wire 12 which for stent purposes may be formed of a suitably flexible biocompatible metal. The wire coil spring 10 defines generally a cylindrical tubular shape which is radially expandable upon application of outward radial pressure from the interior thereof.

Figures 2, 3:
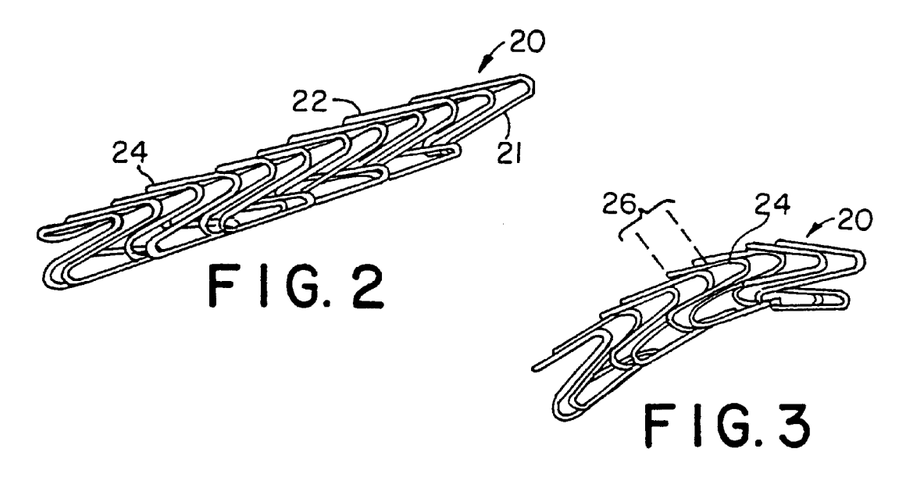
FIG. 2 is a perspective view of the stent of the present invention.
FIG. 3 is a perspective view of the stent of FIG. 1 exhibiting longitudinal flexibility.
Figure 2:
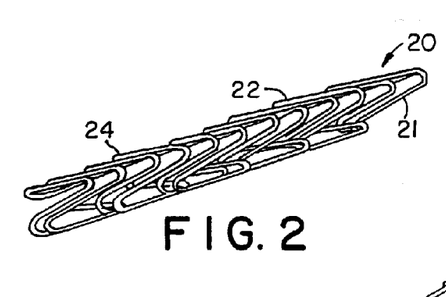
Figure 3:
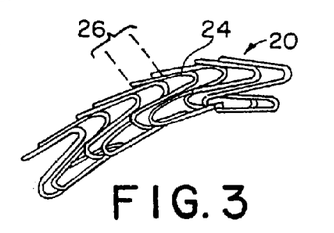

The present invention shown in FIG. 2, improves upon the simple coil spring 10 shown in FIG. 1. However with reference to FIG. 1, certain terminology used hereinthroughout may be defined. As mentioned, the spring defines a generally elongate cylindrically tubular shape lying along a central axis χ. Wire 12 is helically wound, for example against a constant diameter mandrel (not shown), to form a longitudinally extending structure consisting of wire 12 and spaces or pitch 16 therebetween. Each individual winding 14 may be defined as the wire segment traversing one complete revolution around axis $\chi$. As the wire is helically coiled about axis $\chi$, each winding is successively longitudinally spaced from the next adjacent winding by a given distance.

For present purposes, the axial spacing between any point on the wire coil spring 10 to the point defining the next successive winding may be thought of as the pitch 16 of the wire coil spring 10. As so defined, the pitch of the coil spring 10 defines the spacing between windings and therefore the degree of compactness or compression of the wire coil spring 10.

Also with reference to FIG. 1, as the wire coil spring 10 has a generally cylindrical tubular shape, it defines an outside diameter $d_1$ and an inside diameter $d_2$ which would typically differ by twice the diameter $d_3$ of wire 12. Further, wire coil spring 10 generally defines an outer cylindrical surface area along its length which may be thought of as being composed of solid surface portions defined by the outward facing surface of wire 12 itself and open surface portions defined by the spaces or pitch 16 multiplied by the number of wire windings 14. The ratio of open surface space to solid surface space may be varied by varying the so-defined pitch 16 of the wire coil spring 10. A smaller pitch coil, where the windings are more compacted or compressed, would result in an outer surface area having less open space than a coil formed to have greater spacing or pitch between the wire windings.

Having set forth the definitional convention used hereinthroughout, the present invention may be described with reference specifically to FIGS. 2–6. A wire stent 20 of the present invention is shown in FIG. 2. Wire stent 20 is generally in the form of an elongate cylindrically shaped tubular member defining a central open passage 21 therethrough. Stent 20 is formed of multiple windings 24 of a single wire 22 which in the present invention is metallic, preferably tantalum, as such wire exhibits sufficient spring elasticity for purposes which will be described in further detail hereinbelow.

While stent 20 may be formed by helically winding wire 22 much in a manner shown with respect to FIG. 1 to form wire coil spring 10, the present invention contemplates preshaping the wire 22 itself along its length prior to helically coiling the wire.

Figure 4:
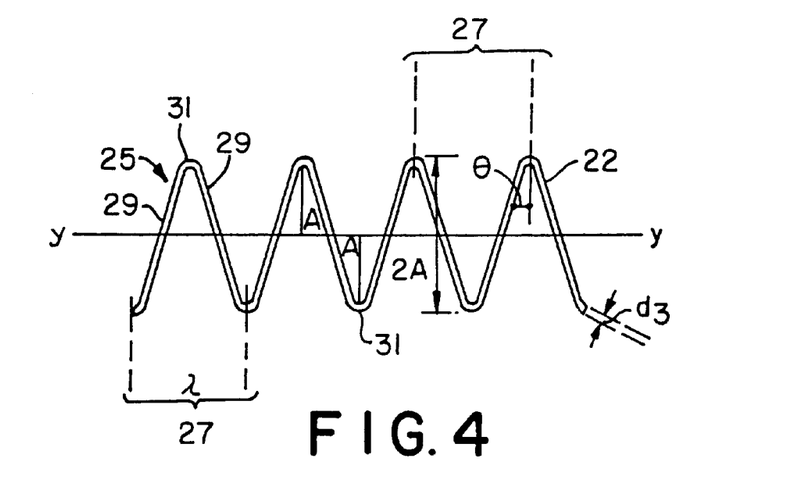
FIG. 4 is a schematic showing of one wave of the wire forming the stent of FIG. 2.

Referring now to FIG. 4, wire 22 in an elongate prehelically coiled configuration may be shaped in a manner having a longitudinally extending wave-like pattern. Wave pattern 25 is defined by a plurality of continuously repeating wave lengths 27 therealong. It has been found advantageously that the waves may take the form specifically shown in FIG. 4 and 5 for optimum results as a wire stent. However, for explanation purposes, the wave-like pattern 25 generally functions mathematically as sinusoidal wave, having a given amplitude A as measured from a central axis y and a peak-to-peak amplitude of 2A. The wave pattern 25 has a uniform preselected period $\lambda$ equal to the transverse extent of a single wave length. The geometry of each wave length 27 is shown in FIG. 4.

The wave-like configuration imparted to wire 22 may be accomplished in a variety of forming techniques. One such technique is to pass wire 22 between the teeth of intermeshed gears (not shown) which would place a generally uniform sinusoidal wave-like crimp along the length of the wire. Other techniques may be used to form the specific shape shown in FIG. 4. Wire 22 may be passed through a pair of gear-like overlapping wheels (not shown) having depending interdigitating pins. By arranging the size, position and spacing of the pins, various wave-like configurations may be achieved. The particular shape shown with reference to FIGS. 4 and 5 has been selected as each wave length 27 includes a pair of non-curved linear sections 29 between curved peaks 31. As will be described with respect to FIG. 5, this configuration allows the waves to be stacked or nested with maximum compactness when the wire is helically wound around a forming mandrel (FIG. 8) into the shape shown in FIG. 2.

Figure 5:
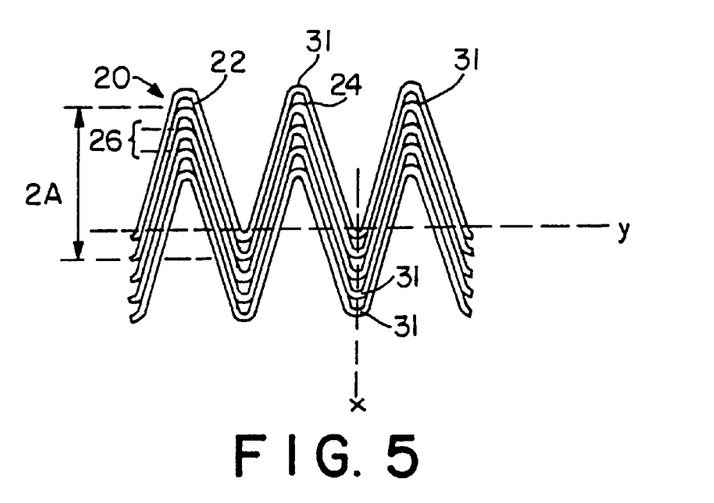
FIG. 5 is a schematic showing of nested longitudinally adjacent waves of the stent of FIG. 2.
Figure 8:
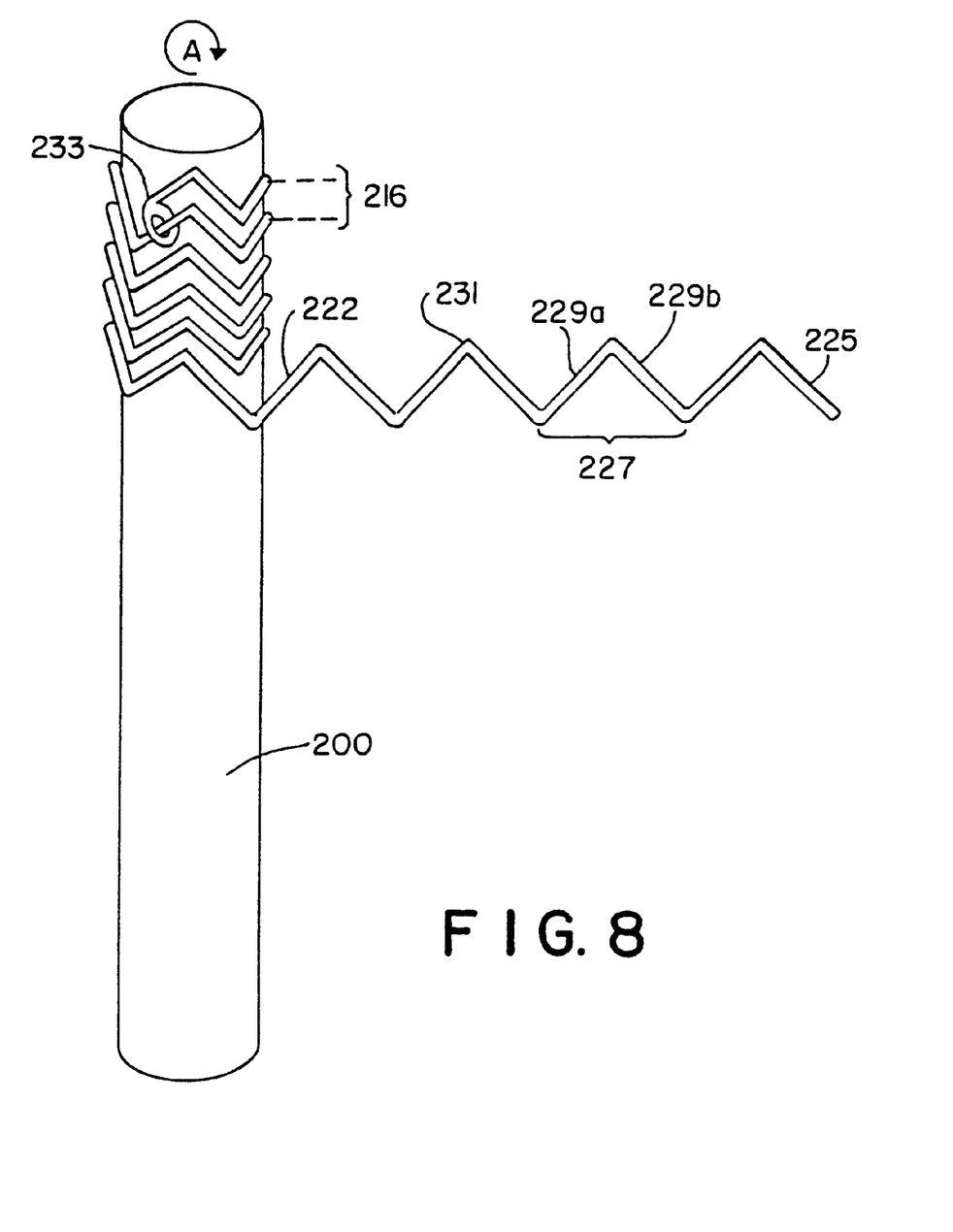
FIG. 8 shows a still further embodiment of a wire used to form a stent of the present invention, partially wound around a forming mandrel.

Referring now to FIG. 5, schematically shown is a portion of stent 20 of FIG. 2 which has been cut once, parallel to the $\chi$ axis and flattened after being wound in a helical fashion such as that described with respect to the wire coil spring 10 of FIG. 1. Wire 22 formed in the manner shown and described with respect to FIG. 4, may be helically wound around an appropriately shaped mandrel (FIG. 8). The width of the mandrel is selected in combination with the frequency and period of the waves forming wire 22 so that upon helical coiling therearound the waves forming each winding 24 are longitudinally stacked or nested within the waves formed by the longitudinally adjacent winding successively spaced therefrom.

As can be seen with respect to FIG. 5, the peaks 31 of the waves of longitudinally adjacent windings 24 are each linearly aligned so that each wave is stacked or nested within the next adjacent wave. In optimum configuration, the spacing or pitch 26 between each longitudinally successive winding 24 is constructed to be minimal. However, nesting or stacking does occur where the pitch or spacing between longitudinally adjacent windings 24 is less than 2A i.e. the peak-to-peak amplitude. As long as the pitch remains less than 2A each longitudinally adjacent winding 24 will be nested within the wave formed by the previously formed winding 24. By minimizing the pitch or spacing 26 between adjacent windings 24, the open space between windings may be minimized. The particular wave-like pattern imparted to wire 22 as shown in FIG. 4 allows particularly tight stacking of longitudinally adjacent windings.

The particular configuration of the stent 20 shown in FIG. 2, provides significant advantages in medical applications. The stent 20 of the present invention is typically implanted by means of a balloon catheter (not shown). The stent 20 in a closed form is held around a deflatable catheter balloon. The stent is then inserted into the lumen and located at the desired position. The shape of the closed stent shown in FIG. 2 permits ease of insertability. As shown in FIG. 3, the stent may be easily bent or flexed along its longitudinal extent. The spacing or pitch 26 of windings 24 facilitate such bending. This helps in the insertion and deployment of the stent through a lumen, as typically body lumens traverse a torturous path through the body which must be followed by the stent which is being deployed therein. Once properly located, the balloon is inflated and the stent is radially expanded for deployment. The balloon is then deflated, and the catheter is removed leaving the expanded stent in place.

Figure 6:
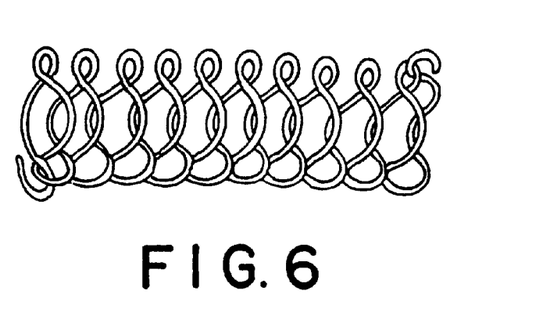
FIG. 6 is a perspective view of the stent of FIG. 2 shown in the open or exposed condition.

The windings of stent 20 in closed condition are tightly nested. The cylindrical surface area formed by the coiled wire has greater wire density, i.e. more of the surface area is composed of solid wire while less of the surface area is composed by open space between the wire windings then in previous non-nested single wire stents. The wire surface area in the closed condition equals the wire surface area in an expanded condition. By maximizing the closed condition wire surface area, even when the stent is expanded such as shown in FIG. 6, the expanded wire surface area is also maximized reducing tissue ingrowth between the expanded windings of the stent. Contrary to a simple coil spring such as that shown in FIG. 1, the stent 20 of the present invention expands without significant foreshortening of the stent or rotation of the ends of the coil. Rather, expansion is achieved by a flattening or elongation of the individual waves of the stent 20. Once the stent is expanded after deployment to a shape shown in FIG. 6, the increased wire surface area as well as the particular shape of the wire provides sufficient radial strength to resist the compressive forces of a blocked, constricted or impinged upon lumen.

Additionally, the above-described benefits of the stent of the present invention are achieved without the necessity of longitudinally overlapping adjacent wire windings. In many prior art stents, the stents include portions of wire windings which are longitudinally overlapped. This increases the wall thickness of the stent thereat and results in a stent which is more difficult to implant in the body lumen by means of a balloon catheter. Also, such stents create an undesirable, more turbulent fluid flow therethrough. The stent of the present invention maximizes wire density, maintains a high degree of flexibility and radial compressive strength without increasing the stent wall thickness beyond the single wire diameter.

EXAMPLE

Mathematically, the geometric analysis of the preferred embodiment of the stent of the present invention may be described as follows with reference to FIGS. 4 and 5.

Each wave length 27 of the wave pattern 25 forming stent 20 is formed to include a straight leg segment 29 with a bend radius at peak 31. The angle at which the helix coils around the center line $\chi$ (FIG. 1) is assumed to be close to 90°, so that the successive windings 24 are positioned to be as close to concentric as possible while still maintaining a helical pattern.

The integer number of waves N per single circumference or single winding follows the equation:

$$N = \frac{\pi D}{\lambda};$$

where D is the diameter of the closed stent and $\lambda$ is the period of a single wave.

The number of helical windings M per stent is defined by the equation:

$$M = \frac{L \sin\theta}{d_3};$$

where L is the overall stent length; $\theta$ is the angle of the straight leg segments 29 with respect the line of amplitude of the wave pattern; and $d_3$ is the wire diameter.

The exterior exposed surface area of the stent is equivalent to the amount of wire packed within a fixed stent length. The total length $L_w$ of wire employed to form the stent follows the equation:

$$L_w = MN\left(4l + 4\left(r + \frac{d_3}{2}\right)\frac{\pi}{180}(90 - \theta)\right)$$

where r is the radius defining the peak curvative; and l is the length of the straight line segment 29 of the wire.

It follows that the projected solid wire area is $L_w d_3$ and the percentage of open space coverage (% open) is given by the equation:

$$\% \text{ OPEN} = 100\left(1 - \frac{L_w d_3}{\pi DL}\right)$$

In a specific example, a stent having the parameters listed in Table I and formed in accordance with the present invention yields a percentage of open space (% open) equivalent to 28.959%.

TABLE I

| | | |
|---|---|---|
| L | Length of Stent | 1.000 in |
| D | Diameter of Closed Stent | 0.157 in |
| $d_3$ | Wire Diameter | 0.010 in |
| r | Radius of Curvative of Peak | 0.020 in |
| N | Number of Waves per Winding | 3 |
| M | Number of Windings per Stent | 22.47 |
| l | Length of Straight Portion of Stent | 0.097 in |

Further, it is found that an expanded stent constructed in accordance with the example set forth above, exhibits superior resistance to pressure P acting upon the stent in a radially compressive manner (FIG. 6). In the present and illustrative example, P has been has been determined, both mathematically and empirically, to be 10 psi.

It is further contemplated that the stent-of the present invention may be modified in various known manners to provide for increased strength and support. For example the end of wire 22 may be looped around an adjacent wave or extended to run along the length of the stent. The wire may be welded to each winding to add structural support such as is shown in U.S. Pat. No. 5,133,732. Also, each windings may be directly welded to the adjacent winding to form a support spine such as shown in U.S. Pat. No. 5,019,090.

Figure 7:
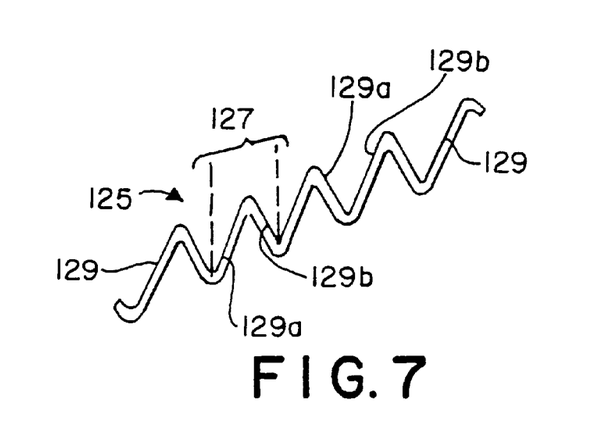
FIG. 7 shows a portion of a further embodiment of a wire used to form a stent in accordance with the present invention.

Further, as mentioned above, wire 22 is helically wound around a mandrel to form the helical pattern shown in FIG. 1. While the angle at which the helix coils around the mandrel is quite small, a certain angle must be imparted to the uniform windings to form a coil. It is further contemplated that a helix-like winding may be formed by concentrically wrapping a wave pattern around the mandrel where the length of the sides of each wave are unequal. As shown in FIG. 7 a wave pattern 125 may be formed having leg segments 129 of uneven length. Wave pattern 125 includes individual wave lengths 127 having a first leg segment 129a and a second leg segment 129b. Leg segment 129a is constructed to be shorter than leg segment 129b. Thus wave pattern 125 has a step-type shape so that upon winding around a mandrel, the windings 124 coil in a helical-like fashion therearound. This provides a lengthwise extent to the coil without having to impart a helical wrap thereto. Forming the stent length in this manner may tend to result in better flow characteristics through the stent in use.

Other modifications which are within the contemplation of the present invention may be further described. FIG. 8 shows a wire 222 which has been preformed to have a wave pattern 225 which is generally triangular in shape. This wave pattern 225 includes individual wave lengths 227 having straight leg segments 229a and 229b which meet at an apex 231. Wire 222 so formed, may be wound around a mandrel 200. As the individual wave lengths 227 nest in a manner above described, the apices 231 of the wave length 227 are longitudinally aligned.

The winding of wire 222 around mandrel 200 takes place in the following manner. The formed wire 222 is held in position while the mandrel is rotated in the direction of arrow A, thereby coiling the wire 222 around mandrel 200.

The spacing or pitch 216 is created by subsequent vertical movement of the of the formed wire 222 along mandrel 200 while rotation thereof is taking place. When the winding is complete, the ends 233 of the wire 222 may be "tied off" by looping the end 233 around the next longitudinally adjacent winding.

While in the embodiment shown above, the amplitude of each wave is relatively uniform, it is contemplated that the wire could be formed to have waves of varied amplitude. For example, the wire could be formed so that at the ends of the wound stent the amplitude of the waves is relatively small while in the central portion of the stent the amplitude is relatively large. This provides a stent with a more flexible central section and more crush-resistant ends.

Figure 9:
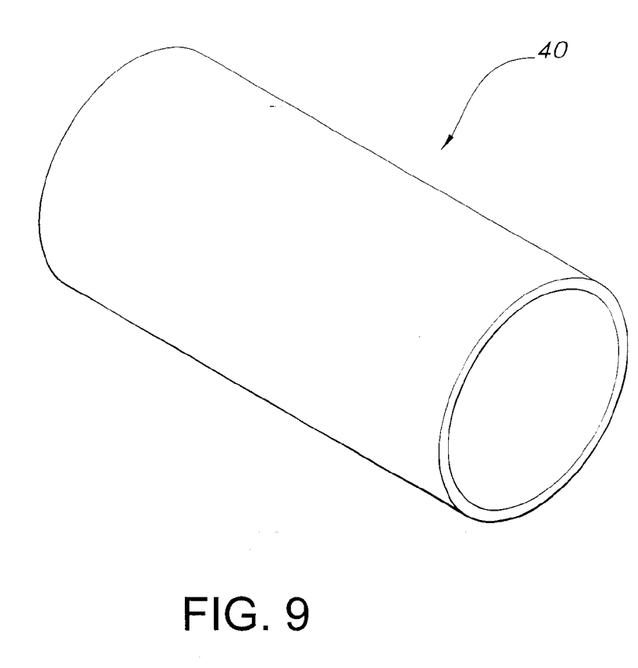
FIG. 9 shows a membrane covering which may be employed in combination with the stent of the present invention.

In certain situations the stent of the present invention may include a membrane covering 40 (FIG. 9) which would cover the entire stent. The wire surface of the stent would serve as a support surface for the membrane covering. The membrane covering would act as a further barrier to tissue ingrowth. Any membrane covering may be employed with the present invention such as a fabric or elastic film. Further, this membrane covering may be completely solid or may be porous. In addition, as above described, employing a formed wire having varied amplitude where the amplitude of the wire is smaller at the ends of the stent would help support the membrane covering as the crush-resistant ends would serve as anchors to support the membrane covering with little support necessary at the more flexible central section of the stent.

Various changes to the foregoing described and shown structures would not be evident to those skilled in the art. Accordingly, the particularly disclosed scope of the invention is set forth in the following claims.

What is claimed is:

1. An intraluminal device comprising:
   an elongate tubular body formed of wire defining a plurality of non-overlapping nested wire waves spaced along the length of said body; and
   a covering supported by said tubular body.
2. An intraluminal device of claim 1 wherein said covering is porous.
3. An intraluminal device of claim 1 wherein said covering is solid.
4. An intraluminal device of claim 1 wherein said covering is elastic.
5. An intraluminal device of claim 1 wherein said covering is formed from a membrane.
6. An intraluminal device of claim 1 wherein said covering is generally cylindrical.
7. An intraluminal device of claim 6 wherein said covering is supported continuously along said tubular body.
8. An intraluminal device of claim 1 wherein said covering forms a barrier inhibiting tissue ingrowth.
9. An intraluminal device of claim 1 wherein said covering is formed of a film.
10. An intraluminal device of claim 9 wherein said film is porous.
11. An intraluminal device of claim 9 wherein said film is elastic.
12. An intraluminal device of claim 1 wherein said covering is formed of a fabric.
13. An intraluminal device of claim 12 wherein said fabric is porous.
14. An intraluminal device of claim 1 wherein said wire includes a single continuous, helically wound wire.
15. An intraluminal device of claim 1 wherein said elongate tubular body is expandable from a contracted condition to an expanded condition without significant foreshortening of said tubular body.
16. An intraluminal device of claim 15 wherein said tubular body is expandable upon application of a radially outwardly directed force.
17. An intraluminal device of claim 15 wherein said tubular body is balloon expandable.
18. A composite intraluminal device comprising:
    an elongate tubular wire-formed body, the wire forming said body being configured into a plurality of waves, each wave of said plurality having a wave peak and a pair of leg segments extending from said peak, said waves being arranged in spaced non-overlapping longitudinal succession such that the peak of one said waves is nested within the next adjacent longitudinally successive wave; and
    a covering supported by said wire formed body.
19. A composite intraluminal device of claim 18 wherein said leg segments of each pair are of generally equal length.
20. A composite intraluminal device of claim 18 wherein at least one wave includes leg segments of unequal length.
21. A composite intraluminal device of claim 18 wherein each of said waves include leg segments of generally uniform unequal length.
22. A composite intraluminal device of claim 18 wherein said plurality of waves are non-overlappingly spaced at a sufficiently small pitch so as to define a compact configuration.
23. A composite intraluminal device of claim 18 wherein said tubular body includes plural wire windings formed into a wave-like pattern defining said waves, said windings being longitudinally spaced therealong, the waves of one winding being nested within the waves of the next adjacent winding.
24. A composite intraluminal device of claim 18 wherein said windings are uniformly spaced apart.
25. A composite intraluminal device of claim 23 wherein said wire windings are formed by a single continuous, helically wound wire.
26. A composite intraluminal device of claim 18 wherein said pair of leg segments and said wave peak define a wave amplitude.
27. A composite intraluminal device of claim 26 wherein said amplitude of said waves is generally uniform.
28. A composite intraluminal device of claim 26 wherein said amplitude of said waves varies along the length of said tubular body.
29. A composite intraluminal device of claim 26 wherein said amplitude of said waves at a central location of said tubular body is greater than said amplitude of the waves at the ends thereof.
30. A composite intraluminal device of claim 18 wherein said pair of leg segment and said wave peak defines a wave length.
31. A composite intraluminal device of claim 30 wherein said wave length of said waves are uniform.
32. A composite intraluminal device of claim 30 wherein said wavelength of said waves are non-uniform.
33. A composite intraluminal device of claim 25 wherein said helically wound wire includes a wire end and wherein said wire end is supported by at least one wire winding.
34. A composite intraluminal device of claim 33 wherein said wire end is secured across plural wire windings.
35. A composite intraluminal device of claim 33 wherein said wire end is welded to each of said plural wire windings.
36. A composite intraluminal device of claim 33 wherein said wire end is secured to the next adjacent wire winding.
37. A composite intraluminal device of claim 36 wherein said wire end is looped about said next adjacent wire winding.

38. A method of forming an intraluminal device comprising the steps of:
   providing a generally tubular membrane covering; and
   supporting said membrane covering with an elongate tubular stent body, said stent body being formed of wire defining a wave-like pattern including a plurality of wire waves which are non-overlappingly nested along the length of said body.

39. A method of claim 38 wherein said membrane covering is a fabric.

40. A method of claim 38 wherein said membrane covering is a film.

41. A method of claim 38 wherein said membrane covering is porous.

42. A method of claim 38 wherein said membrane covering is non-porous.

43. A method of claim 38 wherein said membrane covering is elastic.

44. An intraluminal device comprising:
   an elongate tubular covering; and
   an elongate tubular body formed from a series of individual helically shaped wires, said wires defining a plurality of non-overlapping nested waves along the length of said tubular body, said helically shaped wires being joined by said tubular covering.

45. An intraluminal device of claim 44 wherein said non-overlapping nested waves form a substantially uniform wave-like pattern.

46. An intraluminal device of claim 44 wherein said tubular body has a substantially uniform diameter.

47. An intraluminal device of claim 45 wherein said wave-like pattern is generally sinusoidal.

48. An intraluminal device of claim 44 wherein said at least one of said individual wires defines a wave having a peak and a pair of leg segments extending from said peak, wherein said leg segments are of unequal length.

49. An intraluminal device of claim 45 wherein said wave-like pattern defines a sufficiently small pitch so as to define a compact configuration.

50. An intraluminal device of claim 44 wherein said individual helically shaped wires define a wave-like pattern with substantially uniform wave amplitude.

51. An intraluminal device of claim 44 wherein said individual helically shaped wires define a wave-like pattern having a varying amplitude.

52. An intraluminal device of claim 45 wherein said covering is a membrane.

53. An intraluminal device of claim 45 wherein said covering is a film.

54. An intraluminal device of claim 53 wherein said film is porous.

55. An intraluminal device of claim 53 wherein said film is solid.

56. An intraluminal device of claim 45 wherein said covering is a fabric.

57. A method of forming a composite intraluminal prosthetic device comprising the steps of
   forming a tubular body from wire, said tubular body defining a plurality of wire-waves which are non-overlappingly nested along the length of said body;
   providing a tubular membrane covering; and
   supporting said membrane covering with said tubular body.

58. A method of claim 57 wherein said forming step includes:
   providing an elongate wire;
   configuring said elongate wire to have a plurality of successive said wire waves; and
   arranging said successive wire waves in said non-overlapping rested arrangement.

59. A method of claim 58 wherein said arranging step includes:
   helically winding said configured wire.

60. A method of claim 58 wherein said configuring step includes:
   configuring said elongate wire to have uniform wire waves.

61. A method of claim 60 wherein said configuring step includes:
   configuring said elongate wire to have non-uniform waves.

62. A method of claim 59 wherein said helically winding step includes:
   winding said wire to define uniform spacing between adjacent wire windings.

63. A method of claim 59 wherein said helically winding step includes
   winding said wire to define non-uniform spacing between adjacent wire windings.

64. An intraluminal composite device comprising
   an elongate stent formed of wire, said wire being arranged in a helical configuration with a number of windings, said stent including plural wire waves wherein each wave includes a peak, the wave peak of one winding being nested into a wave of an adjacent winding; and
   a membrane being supported by said stent so as to maintain flexibility of said stent.

65. An intraluminal composite device of claim 64 wherein said membrane includes a cover for covering a surface of said stent.

66. An intraluminal composite device of claim 64 wherein said cover is solid.

67. An intraluminal composite device of claim 64 wherein said cover is porous.

68. An intraluminal composite device of claim 64 wherein adjacent wire windings are interconnected.

69. An intraluminal device of claim 64 wherein said adjacent wire windings are interconnected by a support.

70. An intraluminal device of claim 68 wherein said support is a spine.

71. An intraluminal device of claim 68 wherein said wire windings are interconnected by an end of said wire.

72. An implantable intraluminal prosthesis comprising:
   an elongate tubular body defined by at least one element forming a plurality of non-overlapping nested waves spaced along the length of said body.

73. An implantable intraluminal prosthesis of claim 72 wherein said non-overlapping nested waves form a substantially uniform wave-like pattern.

74. An implantable intraluminal prosthesis of claim 72 wherein said tubular body has a substantially uniform diameter.

75. An implantable intraluminal prosthesis of claim 73 wherein said wave-like pattern is generally sinusoidal.

76. An implantable intraluminal prosthesis of claim 72 wherein said a least one of said waves has a peak and a pair of leg segments extending from said peak, wherein said leg segments are of unequal length.

77. An implantable intraluminal prosthesis of claim 73 wherein said wave-like pattern defines a sufficiently small pitch so as to define a compact configuration.

78. An implantable intraluminal prosthesis of claim 72 wherein said waves define a wave-like pattern with substantially uniform wave amplitude.

79. An implantable intraluminal prosthesis of claim 72 wherein said waves define a wave-like pattern having a varying amplitude.

80. An implantable intraluminal prosthesis of claim 72 further including a covering supported by said tubular body.

81. An implantable intraluminal prosthesis of claim 80 wherein said covering is a membrane.

82. An implantable intraluminal prosthesis of claim 72 wherein said tubular body is formed by wire waves.

83. An implantable intraluminal prosthesis of claim 82 wherein adjacent wire waves are interconnected.

84. An implantable intraluminal prosthesis of claim 83 wherein said adjacent wire waves are interconnected by a support.

85. An implantable intraluminal prosthesis of claim 82 wherein said wire waves are joined by a covering.

* * * * *

UNITED STATES PATENT AND TRADEMARK OFFICE
CERTIFICATE OF CORRECTION

PATENT NO.    : 6,319,277 B1
DATED         : November 20, 2001
INVENTOR(S)   : Rudnick et al.

It is certified that error appears in the above-identified patent and that said Letters Patent is hereby corrected as shown below:

Delete Drawing Sheets 1-3 and insert Drawing Sheets 1-4 attached.

Signed and Sealed this

Twenty-ninth Day of April, 2003

JAMES E. ROGAN
*Director of the United States Patent and Trademark Office*